United States Patent [19]
Wachter et al.

[11] Patent Number: 5,968,488
[45] Date of Patent: Oct. 19, 1999

[54] DEODORIZING PREPARATIONS CONTAINING CATIONIC BIOPOLYMERS, ALUMINUM HYDROCHLORATE AND ESTERASE INHIBITORS

[75] Inventors: Rolf Wachter, Duesseldorf; Rudolf Lehmann, Leichlingen; Claudia Panzer, Grevenbroich, all of Germany

[73] Assignee: Henkel Kommanditgesellschaft auf Aktien, Duesseldorf, Germany

[21] Appl. No.: 09/066,358

[22] PCT Filed: Oct. 21, 1996

[86] PCT No.: PCT/EP96/04563

§ 371 Date: Apr. 28, 1998

§ 102(e) Date: Apr. 28, 1998

[87] PCT Pub. No.: WO97/16164

PCT Pub. Date: May 9, 1997

[51] Int. Cl.⁶ .............. A61K 7/32; A61K 7/38; A61K 7/00; C08B 37/08
[52] U.S. Cl. .............. 424/65; 424/68; 424/400; 424/401; 536/20
[58] Field of Search .............. 424/65, 68, 400, 424/401; 536/20

[56] References Cited

U.S. PATENT DOCUMENTS 5,411,731  5/1995  Tanaka et al. ............... 424/78.02
5,442,048  8/1995  Meister et al. ............... 536/20

FOREIGN PATENT DOCUMENTS

| 0 382 150 | 8/1990 | European Pat. Off. . |
| 63/290808 | 11/1988 | Japan . |
| 71 635 | 1/1975 | Luxembourg . |
| WO87/06827 | 11/1987 | WIPO . |
| WO91/05808 | 5/1991 | WIPO . |
| WO91/07165 | 5/1991 | WIPO . |

OTHER PUBLICATIONS

W. Umbach, "Kosmetik", Thieme Verlag, p. 141, et seq., New York (1998).

Gesslein, et al., HAPPI 27: 57 (1990).

O. Skaugrud, Drug Cosm. Ind. 148: 24 (May, 1991).

E. Onsoyen, et al., Seifen–Öle–Fette–Wachse 117: 633–37 (1991).

Tronnier, et al, J. Soc. Cosm. Chem. 24: 281–290 (1973).

Graham, et al., J. Pharm. Pharmacol. 26: 531–534 (1974).

*Primary Examiner*—Shelley A. Dodson
*Attorney, Agent, or Firm*—Ernest G. Szoke; Wayne C. Jaeschke; Steven J. Trzaska

[57] ABSTRACT

A deodorant composition containing: (a) a cationic biopolymer; (b) an aluminum chlorohydrate; and (c) an esterase inhibitor.

19 Claims, No Drawings

DEODORIZING PREPARATIONS CONTAINING CATIONIC BIOPOLYMERS, ALUMINUM HYDROCHLORATE AND ESTERASE INHIBITORS

BACKGROUND OF THE INVENTION

Field of the Invention

This invention relates to deodorizing formulations containing cationic biopolymers, aluminium chlorohydrate and esterase inhibitors.

Discussion of Related Art

In the field of personal hygiene, deodorants are used to eliminate troublesome body odors. Body odors are formed by the bacterial decomposition of basically odorless perspiration, particularly in the damp underarm regions or under similar conditions favorable to microorganism growth. Body odors can be masked by suitable perfumes. They can also be controlled by using formulations which inhibit the actual secretion of perspiration or its decomposition (so-called antihydrotics, antiperspirants or antitranspirants). Typical examples of such substances are aluminium compounds, such as aluminium sulfate or aluminium chlorohydrate, zinc salts and citric acid compounds. An overview of these agents was published, for example, in Umbach (Ed.), "Kosmetik", pages 141 et seq., Thieme Verlag, Stuttgart, 1988.

However, it is clear from everyday living that the problem of odor inhibition, particularly in heat or in the event of bodily activity, has by no means been completely solved. Commercial products are unable permanently to suppress the secretion of perspiration or the formation of odors. Instead, their inhibiting effect is of limited duration and is also dependent on the extent to which perspiration is secreted. Accordingly, there is a constant need for improved products which minimize the secretion of perspiration and reduce the formation of body odors and which, at the same time, show increased dermatological compatibility, i.e. reduced irritation potential towards particularly sensitive skin. The problem addressed by the present invention was to provide such products.

DESCRIPTION OF THE INVENTION

The present invention relates to deodorizing formulations containing (a) cationic biopolymers,
(b) aluminium chlorohydrate and/or
(c) esterase inhibitors.

The use of aluminium chlorohydrates and esterase inhibitors of the triethyl citrate type for producing deodorizing and/or antiperspirant compositions is known from the prior art. It has surprisingly been found that cationic biopolymers, preferably of the chitosan type, inhibit the activity of esterase-producing bacteria and that a synergistic deodorizing effect is obtained in conjunction with the two components mentioned above. The biopolymers have a bacteriostatic effect, i.e. the population of the germs in question is controlled, but not destroyed in order not to impair the biological equilibrium of the dermal flora. At the same time, the use of the cationic biopolymers leads to an improvement in the dermatological compatibility of the products.

Cationic biopolymers

Cationic biopolymers suitable for use as component (a) are preferably partly deacetylated chitins with various molecular weights which contain the—idealized—monomer unit (I):

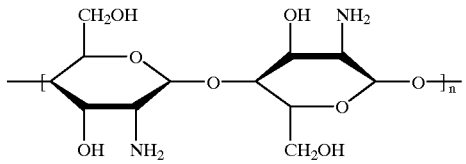

In contrast to most hydrocolloids, which are negatively charged at biological pH values, the chitosans preferably used are cationic compounds under these conditions. The positively charged chitosans are capable of interacting with oppositely charged surfaces and, accordingly, are used in cosmetic hair-care and body-care formulations. Overviews on this subject have been published, for example, by B. Gesslein et al. in HAPPI 27 57 (1990), by O Skaugrud in Drug Cosm. Ind. 148, 24 (1991) and by E. Onsoyen et al. in Seifen-Öle-Fette-Wachse 117 633 (1991). Chitosans are produced from chitin, preferably from the shell remains of crustaceans which are available in large quantities as inexpensive raw materials. Normally, the chitin is first deproteinized by addition of bases, demineralized by addition of mineral acids and, finally, deacetylated by addition of strong bases, the molecular weights being spread over a broad range. Chitosans subsequently degraded with hydrogen peroxide are preferred. Corresponding processes for the production of—microcrystalline—chitosan are described, for example, in WO 91105808 (Firextra Oy) and in EP-B1 0 382 150 (Hoechst).

Aluminium chlorohydrate

The aluminium chlorohydrates of component (b) are colorless hygroscopic crystals which readily coalesce in air and which accumulate during the concentration of aqueous aluminium chloride solutions by evaporation. Aluminium chlorohydrate is used for the production of antiperspirant and deodorizing formulations and probably acts by contracting or blocking the sweat glands by protein precipitation and/or removal of moisture [cf. J. Soc. Cosm. Chem. 24, 281 (1973)]. An aluminium chlorohydrate which corresponds to the formula $[Al_2(OH)_5Cl]*2.5H_2O$ is commercially available under the name of Locrono from Hoechst AG of Frankfurt, FRG. This aluminium chlorohydrate is particularly preferred for the purposes of the invention [cf. J. Pharm. Pharmacol. 26, 531(1974)].

Esterase inhibitors

When perspiration is present in and around the underarm region, enzymes (esterases) which cleave esters and thus emit odor-forming substances are activated by bacteria and released into the extracellular space. The esterase inhibitors of component (c), preferably trialkyl citrates, such as trimethyl citrate, tripropyl citrate, tributyl citrate and, in particular, triethyl citrate (Hydagen® CAT, Henkel KGaA, Düsseldorf, FRG) inhibit the enzyme activity and thus reduce odor formation. The free acid is probably released by the cleavage of the citric acid ester, reducing the pH value on the skin to such an extent that the enzymes are blocked.

Other substances suitable for use as esterase inhibitors are dicarboxylic acids and esters thereof such as, for example, glutaric acid, glutaric acid monoethyl ester, glutaric acid diethyl ester, adipic acid, adipic monoethyl ester, adipic acid diethyl ester, malonic acid and malonic acid diethyl ester, hydroxycarboxylic acids and esters thereof such as, for example, citric acid, malic acid, tartaric acid or tartaric acid diethyl ester. 5-Chloro-2-(2,4-dichlorophenoxy)-phenol, which is marketed by Ciba-Geigy of Basel, Switzerland under the name of Irgasan®, has also proved to be particularly effective.

Commercial Applications

Cationic biopolymers have proved to be bacteriostatic for the described application. Accordingly, the present invention also relates to their use—either on their own or in the form of mixtures with aluminium chlorohydrates and/or esterase inhibitors—for the production of deodorizing formulations.

In one preferred embodiment of the invention, the compositions according to the invention may contain components (a), (b) and (c) advantageously in the following quantities, based on their solids content:

(a) 0.01 to 50, preferably 2 to 5% by weight of cationic biopolymers, (b) 1 to 50, preferably 10 to 50% by weight of aluminium chlorohydrate and (c) 0.01 to 20, preferably 1 to 5% by weight of esterase inhibitors, with the proviso that the quantities shown add up to 100% by weight. The above figures apply to the active substance content of the components.

Germ-inhibiting agents

The formulations according to the invention may contain known germ inhibitors as further additives. Typical examples are preservatives which act specifically against gram-positive bacteria such as, for example, 2,4,4'-trichloro-2'-hydroxydiphenyl ether, chlorhexidine (1,6-di-(4-chlorophenyl-biguanido)-hexane) or TCC (3,4,4'-trichlorocarbanilide). Numerous perfumes and essential oils also have antimicrobial properties. Typical examples are the active substances eugenol, menthol and thymol in nettle, mint and thyme oil. An interesting natural deodorant is the terpene alcohol farnesol (3,7,1 1-trimethyl-2,6,10-dodecatrien-1-ol) which is present in linden blossom oil and which smells of lily-of-the-valley. Glycerol monolaurate has also been successfully used as a bacteriostatic agent. The percentage content of the additional germ-inhibiting agents is normally about 0.1 to 2% by weight, based on the solids component of the formulations.

Auxiliaries and additives

To enable the active substances to be applied to the skin in a measured, economical, convenient and cosmetically attractive manner, they are normally incorporated in formulation bases. The most important of these are alcoholic and/or aqueous/alcoholic solutions, emulsions, gels, oils, waxtfat compounds, stick preparations and powders. Thus, the formulations according to the invention may contain, for example, up to 60% by weight of lower aliphatic alcohols, preferably ethanol, and up to 60% by weight of organic acids, such as glycolic acid for example. Other suitable auxiliaries and additives include superfatting agents, emulsifiers, antioxidants, talcum, silica (for example as a support for the aluminium chlorohydrate) and perfume oils, essential oils, dyes and—for spray applications—propellent gases such as, for example, propane and/or butane. The formulations are preferably marketed as rollers (roll-on emulsions), sticks, deodorant sprays or pump sprays.

EXAMPLES

I. Ingredients

A) Cationic biopolymer of the chitosan type (Hydagen® CMF, Henkel KGaA); 1% by weight in 0.4% by weight aqueous glycolic acid B) Aluminium chlorohydrate (Locron® L, Hoechst AG)

C) Triethyl citrate (Hydagen® CAT, Henkel KGaA)

II. Performance tests

The effectiveness of the formulations according to the invention was representatively determined as their esterase-inhibiting effect. To this end, the residual activity of the test mixtures after acting on the esterase for 15 minutes in quantities of 2000 ppm at pH 6 was determined parallel to an uninhibited esterase (standard=100%). Formulations F1, F2, F4, F6 and F7 correspond to the invention while formulations F3, F5 and F8 are intended for comparison. The results are set out in Table 1 below (quantities in % by weight).

TABLE 1

| Components | Formulations and esterase inhibition | | | | | | | |
|---|---|---|---|---|---|---|---|---|
| | F1 | F2 | F3 | F4 | F5 | F6 | F7 | F8 |
| A | 4 | 4 | — | 4 | — | 4 | 4 | — |
| B | 50 | 10 | 50 | — | — | 50 | — | 50 |
| C | 6 | 5 | — | — | 5 | — | 5 | 5 |
| Ethanol | 20 | 20 | 20 | 20 | 20 | — | 20 | 20 |
| Glycolic acid | 0.016 | 0.016 | — | 0.016 | — | 0.016 | 0.016 | — |
| Farnesol | — | 1 | — | — | — | — | — | — |
| Water | | | | to 100 | | | | |
| Esterase activity [%] | 30 | 28 | 100 | 78 | 77 | 73 | 75 | 75 |

We claim:

1. A deodorant composition comprising:

(a) a cationic biopolymer;

(b) an aluminum chlorohydrate; and (c) an esterase inhibitor.

2. The composition of claim 1 wherein the cationic biopolymer is present in the composition in an amount of from 0.01 to 50% by weight, based on the weight of the composition.

3. The composition of claim 1 wherein the aluminum chlorohydrate is present in the composition in an amount of from 1 to 50% by weight, based on the weight of the composition.

4. The composition of claim 1 wherein the esterase inhibitor is present in the composition in an amount of from 0.01 to 20% by weight, based on the weight of the composition.

5. The composition of claim 1 wherein the esterase inhibitor is a trialkyl citrate.

6. The composition of claim 1 further comprising a germ-inhibiting agent selected from the group consisting of gram-positive bacteria, eugenol, menthol, thymol, farnesol, glycerol monolaurate, and mixtures thereof.

7. The composition of claim 6 wherein the germ-inhibiting agent is present in the composition in an amount of from 0.1 to 2% by weight, based on the weight of the composition.

8. The composition of claim 1 further comprising an additive selected from the group consisting of lower aliphatic alcohols, organic acids, superfatting agents, emulsifiers, antioxidants, talcum, silica, perfume oils, essential oils, dyes, and mixtures thereof.

9. The composition of claim 8 wherein the additive is present in the composition in an amount of up to 60% by weight, based on the weight of the composition.

10. A deodorant composition comprising:
   (a) from 2 to 5% by weight of a cationic biopolymer;
   (b) from 10 to 50% by weight of aluminum chlorohydrate; and
   (c) from 1 to 5% by weight of a trialkyl citrate, all weights being based on the weight of the composition.

11. A process for enhancing the deodorizing effectiveness of a deodorant composition based on aluminum chlorohydrate and an esterase inhibitor comprising adding an effective amount of a cationic biopolymer to the deodorant composition.

12. The process of claim 11 wherein the cationic biopolymer is added to the composition in an amount of from 0.01 to 50% by weight, based on the weight of the composition.

13. The process of claim 11 wherein the aluminum chlorohydrate is present in the composition in an amount of from 1 to 50% by weight, based on the weight of the composition.

14. The process of claim 11 wherein the esterase inhibitor is present in the composition in an amount of from 0.01 to 20% by weight, based on the weight of the composition.

15. The process of claim 11 wherein the esterase inhibitor is a trialkyl citrate.

16. The process of claim 11 further comprising adding an effective amount of a germ-inhibiting agent selected from the group consisting of gram-positive bacteria, eugenol, menthol, thymol, farnesol, glycerol monolaurate, and mixtures thereof, to the deodorant composition.

17. The process of claim 16 wherein the germ-inhibiting agent is added in an amount of from 0.1 to 2% by weight, based on the weight of the composition.

18. The process of claim 11 further comprising adding an effective amount of an additive selected from the group consisting of lower aliphatic alcohols, organic acids, superfatting agents, emulsifiers, antioxidants, talcum, silica, perfume oils, essential oils, dyes, and mixtures thereof, to the deodorant composition.

19. The process of claim 18 wherein the additive is added in an amount of up to 60% by weight, based on the weight of the composition.

* * * * *